United States Patent
Kim et al.

(10) Patent No.: US 11,040,999 B2
(45) Date of Patent: *Jun. 22, 2021

(54) ANGIOGENESIS-INHIBITING PEPTIDE AND COMPOSITION FOR PREVENTING AND TREATING ANGIOGENESIS-RELATED DISEASE COMPRISING SAME AS ACTIVE INGREDIENT

(71) Applicant: AVIXGEN INC., Seoul (KR)

(72) Inventors: Young Myeong Kim, Gangwon-do (KR); Yi Yong Baek, Gyeonggi-do (KR); Won Jin Park, Gyeonggi-do (KR); Jeong Hun Kim, Seoul (KR); Dong Hyun Jo, Seoul (KR)

(73) Assignee: AVIXGEN INC., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/777,541

(22) PCT Filed: Jul. 5, 2016

(86) PCT No.: PCT/KR2016/007246
§ 371 (c)(1),
(2) Date: May 18, 2018

(87) PCT Pub. No.: WO2017/099319
PCT Pub. Date: Jun. 15, 2017

(65) Prior Publication Data
US 2019/0315803 A1    Oct. 17, 2019

(30) Foreign Application Priority Data
Dec. 10, 2015 (KR) .......... 10-2015-0175853

(51) Int. Cl.
C07K 5/11 (2006.01)
A61K 38/07 (2006.01)
A61P 27/02 (2006.01)
A61P 35/00 (2006.01)
A61K 38/00 (2006.01)

(52) U.S. Cl.
CPC .......... *C07K 5/1019* (2013.01); *A61P 27/02* (2018.01); *A61P 35/00* (2018.01); *A61K 38/00* (2013.01)

(58) Field of Classification Search
None
See application file for complete search history.

(56) References Cited

U.S. PATENT DOCUMENTS

2003/0198978 A1* 10/2003 Rozzelle .............. C12N 9/1252
435/6.11

FOREIGN PATENT DOCUMENTS

| EP | 0910571 | 7/2005 |
| KR | 20120094867 | 8/2012 |
| WO | WO 1997/41824 | 11/1997 |

OTHER PUBLICATIONS

Baek et al., "The tetrapeptide Arg-Leu-Tyr-Glu inhibits VEGF-induced angiogenesis," Biochem Biophys Res Commun 463:532-537 (Year: 2015).*
Biosynthesis, "N-Terminal Acetylation Amidation Peptides Chemically Synthesized Aminopeptidases Intracellular," 1 page, (2008), accessed Apr. 25, 2018 (Year: 2008).*
Emerson et al., "Emerging therapies for the treatment of neovascular age-related macular degeneration and diabetic macular edema," Biodrugs 21:245-257 (2007) (Year: 2007).*
Age-Related Macular Degeneration, Merck Manual, accessed Feb. 3, 2020 at URL—merckmanuals.com/professional/eye-disorders/retinal-disorders, pp. 1-6 (2019) (Year: 2019).*
Ng et al., "Targeting angiogenesis, the underlying disorder in neovascular age-related macular degeneration," Can J Ophthalmol 40:352-368 (2005) (Year: 2005).*
Human coagulation factor IX, UnitProt Accession No. P00740, accessed Sep. 16, 2020 at URL: uniprot.org/uniprot/P00740, pp. 1-23. (Year: 2020).*
Adams et al., "Molecular regulation of angiogenesis and lymphangiogenesis," *Nat. Rev. Mol. Cell Biol.*, 8:8464-8478, (2007).
Baek et al., "The tetrapeptide Arg-Leu-Tyr-Glu inhibits VEGF-induced angiogenesis," *Biochem Biophys Res Commun.*, 463(4):532-537, (2015). (Abstract Only).
Cao et al., "Kringle 5 of plasminogen is a novel inhibitor of endothelial cell growth," *J. Biol. Chem.*, 272:22924-22928, (1997).
Carriero et al., "UPARANT: a urokinase receptor-derived peptide inhibitor of VEGF-driven angiogenesis with enhanced stability and in vitro and in vivo potency," *Mol. Cancer Ther.*, 13(5):1092-1104, (2014).
Cook et al., "Angiogenesis inhibitors: current strategies and future prospects," *CA Cancer J. Clin.*, 60:222-243, (2010).
Ferrara et al., "Angiogenesis as a therapeutic target," *Nature*, 438:967-974, (2005).

(Continued)

*Primary Examiner* — Julie Ha
*Assistant Examiner* — Kristina M Hellman
(74) *Attorney, Agent, or Firm* — Norton Rose Fulbright US LLP

(57) ABSTRACT

Disclosed are improved peptides for inhibiting angiogenesis, Ac-RLYE (SEQ ID NO: 1) and R(D)LYE (SEQ ID NO: 6), and a composition for the prevention and treatment of cancers and diseases related to angiogenesis comprising the peptides as an active ingredient. A peptide for inhibiting angiogenesis is disclosed wherein the L-Arg of an N-terminal is acetylated in a peptide consisting of an amino acid sequence of Arg-Leu-Tyr-Glu (SEQ ID NO: 1). A peptide for inhibiting angiogenesis is disclosed wherein L-Arg is substituted with D-Arg in a peptide consisting of the amino acid sequence of Arg-Leu-Tyr-Glu (SEQ ID NO: 6). Methods for using a composition comprising the peptides as active ingredients for the prevention or treatment of diseases (cancer, diabetic retinopathy or senile macular degeneration) caused by excessive angiogenesis are also disclosed. The peptides have a long half-life and are excellent in VEGF-induced angiogenesis inhibitory effect.

13 Claims, 6 Drawing Sheets
Specification includes a Sequence Listing.

(56) References Cited

OTHER PUBLICATIONS

Ferrara et al., "The biology of VEGF and its receptors," *Nat. Med.*, 9:669-676, (2003).
Folkman et al., "Angiogenesis in cancer, vascular, rheumatoid and other disease," *Nat. Med.*, 1:27-31, (1995).
Greenberg et al., "VEGF as an inhibitor of tumor vessel maturation: implications for cancer therapy," *Expert Opin. Biol., Ther.*, 9:1347-1356, (2009).
Hilberg et al., "BIBF 1120: triple angiokinase inhibitor with sustained receptor blockade and good antitumor efficacy," *Cancer Res.*, 68:4774-4782, (2008).
Hu-Lowe et al., "Nonclinical antiangiogenesis and antitumor activities of axitinib (AG-013736), an oral, potent and selective inhibitor of vascular endothelial growth factor receptor tyrosine kinases 1, 2, 3," *Clin. Cancer Res.*, 14:7272-7283, (2008).
Idbaih et al., "Therapeutic application of noncytotoxic molecular targeted therapy in gliomas: growth factor receptors and angiogenesis inhibitors," *Oncologist*, 13:978-992, (2008).
International Search Report and Written Opinion issued in International Patent Application No. PCT/KR2016/007246, dated Oct. 12, 2016.
Isogai et al., "The vascular anatomy of the developing zebrafish: an atlas of embryonic and early larval development," *Dev. Biol.*, 230:278-301, (2001).
Kidd et al., "Fishing for novel angiogenic therapies," *Br. J. Pharmacol.*, 140:585-594, (2003).
Lee et al., "Fractalkine stimulates angiogenesis by activating the Raf-1/MEK/ERK- and PI2K/Akt/eNOS-dependent signal pathways," *Am. J. Physiol. Heart Circ. Physiol.*, 291:H2836-H2846, (2006).
Lee et al., "Impaired wound healing and angiogenesis in eNOS-deficient mice," *Am. J. Physiol.*, 277:H1600-1608, (1999).
Neufeld et al., "Vascular endothelial growth factor (VEGF) and its receptors," *FASEB J*, 13:9-22, (1999).
O'Reilly et al., "Angiostatin: a novel angiogenesis inhibitor that mediates the suppression of metastases by a Lewis lung carcinoma," *Cell.*, 79:315-238, (1994).
Sheppard et al., "Lysyl 4-aminobenzoic acid derivatives as potent small molecule mimetics of plasminogen kringle 5," *Bioorg. Med. Chem. Lett.*, 14:965-966, (2004).
Shibuya, "VEGF-VEGFR Signals in Health and Disease," *Biomol. Ther. (Seoul)*, 22:1-9, (2014).
Smith et al., "Genetic selection for peptide inhibitors of angiogenin," *Proetein Eng. Des Sel.* 21(5):289-294, (2008).
So et al., "Giverin/Cd146 is involved in zebrafish cardiovascular development and tumor angiogenesis," *Genes Cells*, 15:1099-1110, (2010).
Soria et al., "Systematic review and meta-anaylsis of randomized, phase II/III trials adding bevacizumab to platinum-based chemotherapy as first-line treatment in patients with advanced non-small-cell lung cancer," *Ann.Oncol.*, 24:20-30, (2013).
Takahashi et al., "The vascular endothelial growth factor (VEGF)/VEGF receptor system and its role under physiological and pathological conditions," *Clin. Sci. (Lond)*, 109:227-241, (2005).
Verheul et al., "Possible molecular mechanisms involved in the toxicity of angiogenesis inhibition," *Nat. Rev. Cancer*, 7:475-485, (2007).
Wang et al., "Biological activity of bevacizumab, a humanized anti-VEGF antibody in vitro," *Angiogenesis*, 7:335-3345, (2004).
Wedge et al., "ZD6474 inhibits vascular endothelial growth factor signaling, angiogenesis, and tumor growth following oral administration," *Cancer Res.*, 62:4645-4655, (2002).
Yakes et al., "Cabozantinib (XL184), a novel MET and VEGFR2 inhibitor, simultaneously suppresses metastasis, angiogenesis, and tumor growth," *Mol. Cancer Ther.*, 10:2298-2308, (2011).
You et al., "VEGF and c-Met blockade amplify angiogenesis inhibition in pancreatic islet cancer," *Cancer Res.*, 71:4758-4768, (2011).

\* cited by examiner

A. PHOSPHATE-BUFFERED SALINE-PRETREATED CONDITION

B. HUMAN SERUM-PRETREATED CONDITION

ANGIOGENESIS-INHIBITING PEPTIDE AND COMPOSITION FOR PREVENTING AND TREATING ANGIOGENESIS-RELATED DISEASE COMPRISING SAME AS ACTIVE INGREDIENT

CROSS-REFERENCE TO RELATED APPLICATIONS

This application is a national phase application under 35 U.S.C. § 371 of International Application No. PCT/KR2016/007246, filed Jul. 5, 2016, which claims priority to and the benefit of Korean Patent Application No. 10-2015-0175853, filed Dec. 10, 2015. The contents of the referenced patent applications are incorporated into the present application by reference.

SEQUENCE LISTING

The instant application contains a Sequence Listing which has been filed electronically in ASCII format and is hereby incorporated by reference in its entirety.

FIELD OF THE DISCLOSURE

The present invention relates to improved peptides for inhibiting angiogenesis, such as Ac-RLYE (SEQ ID NO: 1) and R(D)LYE (SEQ ID NO: 6), and a composition for preventing and treating an angiogenesis-related disease, which contains the peptide as an active ingredient, and more particularly, to a peptide for inhibiting angiogenesis in which N-terminal Arg is acetylated in a peptide consisting of the sequence of amino acids (Arg-Leu-Tyr-Glu (SEQ ID NO: 1)), a peptide for inhibiting angiogenesis in which L-Arg is substituted with D-Arg in a peptide consisting of the sequence of amino acids (Arg-Leu-Tyr-Glu (SEQ ID NO: 6)), and a technique of preventing and treating a disease (cancer, diabetic retinopathy or senile macular degeneration) caused by excessive angiogenesis using a composition containing these peptides as an active ingredient.

DESCRIPTION OF RELATED ART

Angiogenesis occurs under both normal and pathological conditions and refers to generation of a new blood vessel from an existing blood vessel. All types of angiogenesis occurring under physiological conditions such as embryo development and wound healing and pathological conditions such as cancer growth and the occurrence of retinal diseases are regulated by a balance between angiogenesis-promoting and inhibiting factors. However, abnormal angiogenesis caused by excessive generation and accumulation of angiogenesis-promoting factors under physiological conditions is the cause of several diseases including tumor growth and metastasis, rheumatoid arthritis, diabetic retinopathy and senile macular degeneration.

Angiogenesis is commonly induced by a sequential process of activation, proliferation, migration and tube formation of vascular endothelial cells, which is caused by various angiogenesis-promoting factors. A vascular endothelial growth factor (VEGF) of the angiogenesis-promoting factors serves to induce proliferation, migration and differentiation of endothelial cells by activating various signaling cascades. Under pathological conditions, VEGF induces abnormal angiogenesis to promote the growth of tumor cells and retinal cells and vascular leakage, resulting in the growth and metastasis of tumors, diabetic retinopathy, and senile macular degeneration. Therefore, the onset of the formation of new cancer vessels and retina vessels may be controlled by interfering with the biological activity and signaling transduction of VEGF using a neutralizing antibody and a signaling inhibitor of VEGF. Angiogenesis inhibiting drugs targeting VEGF or a VEGF receptor are excellent therapeutic strategies for effectively controlling pathological (abnormal) angiogenesis-related human diseases.

In recent years, several angiogenesis inhibiting antibodies, proteins and chemicals have been developed for treating excessive angiogenesis-related diseases including tumors, diabetic retinopathy and senile macular degeneration, and have been clinically used. However, side effects such as hypertension and hemorrhage may occur, or therapeutic limitations such as low specificity and bioavailability, antigenicity and inadequate pharmacokinetics have been reported. Generally, a small peptide is easily mass-produced, has no antigenicity, and high solubility and bioavailability, and thus is proposed as a good material for drug development.

Therefore, the inventors have conducted various studies for developing peptides that can effectively inhibit angiogenesis induced by VEGF, resulting in the development of an Arg-Leu-Tyr-Glu (RLYE (SEQ ID NO: 2)) peptide effectively blocking the binding between VEGF receptor-2 and VEGF. This peptide exhibited an activity of effectively inhibiting angiogenesis induced by VEGF, and such activity was confirmed to be very useful as a therapeutic agent for a disease caused by excessive angiogenesis, particularly, cancer.

However, according to additional studies, it was confirmed that the RLYE peptide (SEQ ID NO: 2) is rapidly degraded in blood and do not have a long half-life, which need to be improved. If the half-life can be extended, a sustained effect can be expected, and thus the RLYE peptide (SEQ ID NO: 2) was determined to be more effective in treating a disease caused by excessive angiogenesis (cancer, diabetic retinopathy, or senile macular degeneration). Accordingly, a method for improving the half-life of the RLYE peptide (SEQ ID NO: 2) was studied.

SUMMARY OF THE INVENTION

It is an object of the present invention to provide a novel peptide having effects of preventing and treating excessive angiogenesis-related diseases since it has a sustained angiogenesis inhibitory effect due to a longer half-life.

It is another object of the present invention to provide a composition that contains the peptide as an active ingredient and thus exhibits effects of preventing and treating an angiogenesis-related disease, for example, cancer and retinal diseases.

It is still another object of the present invention to provide a method for preventing and treating an angiogenesis-related disease, for example, cancer and retinal diseases, the method including administering the peptide into a subject.

It is yet another object of the present invention to provide a use of a composition containing the peptide as an active ingredient to exhibit excellent effects in preventing and treating an angiogenesis-related disease, for example, cancer and retinal diseases.

In one aspect, the present invention provides a peptide for inhibiting angiogenesis (Ac-RLYE (SEQ ID NO: 1)) in which N-terminal L-Arg is acetylated in a peptide consisting of a sequence of amino acids Arg-Leu-Tyr-Glu (R-L-Y-E or RLYE (SEQ ID NO: 1)) and a peptide for inhibiting angiogenesis (R(D)LYE (SEQ ID NO: 6)) in which N-terminal L-Arg is substituted with D-Arg in a peptide consisting of a sequence of amino acids Arg-Leu-Tyr-Glu (SEQ ID NO: 6).

The two peptides may inhibit angiogenesis induced by VEGF.

In another aspect, the present invention provides a composition containing at least one of the peptides as an active ingredient to prevent and treat an excessive angiogenesis-related disease.

In still another aspect, the present invention provides a method for treating an angiogenesis-related disease, the method including administering at least one of the peptides to a subject.

In yet another aspect, the present invention provides a method for preventing an angiogenesis-related disease, the method including administering at least one of the peptides to a subject.

In yet another aspect, the present invention provides a use of a composition containing at least one of the peptides as an active ingredient to prevent and treat an angiogenesis-related disease.

The composition for preventing and treating an angiogenesis-related disease of the present invention may be used in preventing and treating one or more diseases selected from the group consisting of tumor growth and metastasis, diabetic retinopathy, senile macular degeneration, rheumatoid arthritis and psoriasis.

In yet another aspect, the present invention provides a composition containing at least one of the peptides as an active ingredient to prevent and treat cancer.

In yet another aspect, the present invention provides a method for treating cancer, the method including administering at least one of the peptides to a subject.

In yet another aspect, the present invention provides a method for preventing cancer, the method including administering at least one of the peptides to a subject.

In yet another aspect, the present invention provides a use of a composition containing at least one of the peptides as an active ingredient to prevent and treat cancer.

The composition for preventing and treating cancer containing the peptide of the present invention may effectively prevent and treat various types of cancer, particularly, solid tumors.

In yet another aspect, the present invention provides a composition containing at least one of the peptides as an active ingredient to prevent and treat diabetic retinopathy.

In yet another aspect, the present invention provides a method for treating diabetic retinopathy, the method including administering at least one of the peptides to a subject.

In yet another aspect, the present invention provides a method for preventing diabetic retinopathy, the method including administering at least one of the peptides to a subject.

In yet another aspect, the present invention provides a use of a composition containing at least one of the peptides as an active ingredient to prevent and treat diabetic retinopathy.

In yet another aspect, the present invention provides a composition containing at least one of the peptides as an active ingredient to prevent and treat senile macular degeneration.

In yet another aspect, the present invention provides a method for treating senile macular degeneration, the method including administering at least one of the peptides to a subject.

In yet another aspect, the present invention provides a method for preventing senile macular degeneration, the method including administering at least one of the peptides to a subject.

In yet another aspect, the present invention provides a use of a composition containing at least one of the peptides as an active ingredient to prevent and treat senile macular degeneration.

The peptide of the present invention may be used in drugs, foods or feed for humans or animals.

Here, the peptide according to the present invention may be formulated according to a standard for formulating a conventional pharmaceutical preparation and a standard for formulating health supplement food of the Korean Food and Drug Administration (KFDA).

The peptide of the present invention may be used as is, or in the form of a salt such as a pharmaceutically acceptable acid-addition salt or a metal complex, for example, a sodium (Na), potassium (K), calcium (Ca), zinc (Zn), or iron (Fe) salt. More specifically, the acid-addition salt may be hydrogen chloride, hydrogen bromide, a sulfate, a phosphate, a maleate, an acetate, a citrate, a benzoate, a succinate, a malate, an ascorbate, or a tartrate.

The peptide of the present invention may be diluted by mixing the oligopeptide with a pharmaceutically acceptable carrier by a conventional method according to an administration method, an administration type and a therapeutic purpose, or encapsulated in a container-like carrier.

When the carrier is used as a diluent, the carrier may be prepared in a formulation such as a powder, granules, injections, a syrup, a solution, tablets, suppositories, pessaries, ointment, cream or aerosol for oral administration or parenteral administration using at least one selected from the group consisting of a saline, a buffer, dextrose, water, glycerol, Ringer's solution, lactose, sucrose, calcium silicate, methyl cellulose and ethanol. However, the carrier is not limited to the above-mentioned types of carriers. Here, the parenteral administration refers to intravitreal, rectal, intravenous, intraperitoneal, intramuscular, intraaortic, transdermal or intranasal administration of an effective ingredient, or inhalation, other than oral administration.

The above-mentioned formulation may be prepared by further adding a filler, an anticoagulant, a lubricant, a wetting agent, a flavoring agent, an emulsifier or a preservative to induce rapid, sustained or extended release of an active ingredient after administration to a mammal. In addition, a dosage may be adjusted according to a patient's condition, administration route and administration type, and it will be obvious to those of ordinary skill in the art that the dosage may vary in a wide range without limitation. Conventionally, it is determined that the peptide of the present invention can be continuously or intermittently administered daily at an experimentally effective amount of approximately 0.5 to 1.0 mg per kg of a body weight.

A peptide of the present invention has a long half-life, and a very excellent VEGF-induced angiogenesis inhibitory effect. Therefore, when the peptide developed in the present invention is used for excessive angiogenesis-related diseases, cancer, diabetic retinopathy or senile macular degeneration, these diseases can be very effectively prevented or treated.

EXAMPLES

Figure 1:
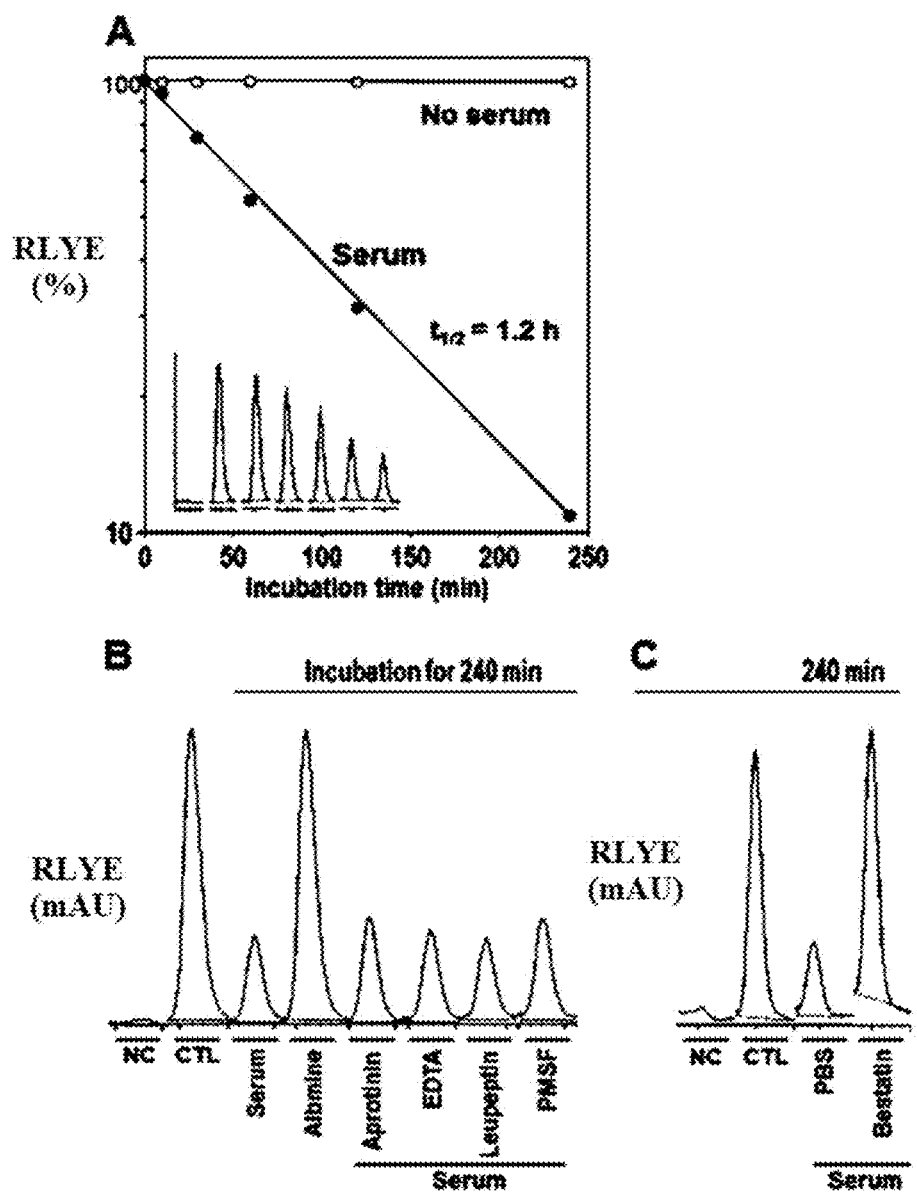
FIG. 1 shows experimental results showing the stability of an RLYE peptide (SEQ ID NO: 2) in human serum. A: An experimental result showing RLYE (SEQ ID NO: 2) stability in human serum and physiological saline (no serum), B: A result showing an effect of a protease inhibitor on RLYE (SEQ ID NO: 2) stability in human serum, C: An experimental result showing an effect of an aminopeptidase B inhibitor, bestatin, on RLYE (SEQ ID NO: 2) stability in human serum. NC: negative control; CTRL: physiological saline control (control).

Hereinafter, the present invention will be described in further detail with reference to examples. These examples are merely provided to illustrate the present invention, and it should not be not construed that the scope of the present invention is not limited by the following examples.

<Confirmation of Effect of Ac-RLYE Peptide (SEQ ID NO: 1) and R(D)LYE (SEQ ID NO: 2) on Anti-Angiogenesis and Treatment of Cancer and Retinal Disease>

1. Experimental Methods 1-1. Experimental Materials and Animal Ethics

All peptides [RLYE (SEQ ID NO: 2), EYLR (SEQ ID NO: 5), Ac-RLYE (SEQ ID NO: 1) (the peptide prepared by acetylating the N-terminus of RLYE (SEQ ID NO: 1)), RLYE-NH$_2$ (SEQ ID NO: 3) (the peptide prepared by amidating the C-terminus of RLYE (SEQ ID NO: 3)), and R(D)LYE (SEQ ID NO: 6) (the peptide prepared by replacing the L-type arginine of RLYE (SEQ ID NO: 6) with D-type arginine)] used in the experiment were synthesized with reference to Peptron, Inc. (Daejeon, Korea). All animal experiments were carried out according to the guidelines of the Ethics Committee for Protection and Use of Experimental Animals of Kangwon National University.

1-2. Peptide Stability Analysis

Serum was separated by centrifugation (tabletop centrifuge, 3000 rpm, 20 min) of blood obtained from a healthy person. The serum was filtrated using a filter (Millipore) with a pore size of 0.22 μM, and then 50 μl of the human serum was mixed with 100 μg of RLYE (SEQ ID NO: 2), R(D)LYE (SEQ ID NO: 6), RLYE-NH$_2$ (SEQ ID NO: 3) or Ac-RLYE (SEQ ID NO: 1) (100 μg/50 μl, PBS, pH 7.4), and incubated by time at a constant temperature of 37° C. A peptide concentration of the sample was calculated by a peak area after the sample was separated by C18 reverse phase high-performance liquid chromatography (HPLC; Vydac protein and peptide C18 column, 0.1% trifluoroacetate in H$_2$O for equilibration, and 0.1% trifluoroacetate in acetonitrile for elution).

1-3. Vascular Endothelial Cell Migration Analysis

Migration analysis for human umbilical cord vascular endothelial cells (HUVECs) was carried out using a Transwell culture plate to which a polycarbonate filter (pore size: 8 μm) with a diameter of 6.5 mm was attached. A surface of the filter was coated with 10 μg of gelatin. Fresh M199 medium (1% fetal bovine serum) containing VEGF (10 ng/ml) was added into a lower compartment of the Transwell plate, HUVECs (1×10$^6$ cells/100 μl) which had reacted with 0.15 nM or 1.5 nM peptides at room temperature for 30 minutes were carefully transferred to an upper compartment of the plate. The resulting HUVECs were cultured in a CO$_2$-constant temperature and humidity chamber for 4 hours, and the cells migrated under the Transwell filter were stained by H&E staining and quantified using an optical microscope.

1-4. Analysis of Tube Formation of Vascular Endothelial Cells

A degree of tube formation of HUVECs was determined using growth factor-reduced Matrigel. 250 μl of the Matrigel (10 mg protein/ml) was added into a 24-well plate to allow polymerization for 30 minutes at 37° C. HUVECs cultured in M199 (1% fetal bovine serum) medium for 6 hours were carefully transferred onto the Matrigel in the culture plate at a density of 2×10$^5$ cells/well, and VEGF (10 ng/ml) were cultured alone or with peptides (0.15 nM) at 37° C. for 20 hours. Meanwhile, peptides that were reacted in PBS or fresh human serum for 3 hours were also used. The degree of tube formation of HUVECs was visualized using an inverted phase-contrast microscope, and a length of the formed tube was measured and quantified by Image-Pro Plus version 4.5 (Media Cybernetics, San Diego, Calif.).

1-5. Human Colon Cancer (HCT116) Xenografted Mouse Model

Human colon cancer cells (HCT116, $1\times10^7$ cells/100 µl) were subcutaneously injected into the left side of a nude mouse (BALB/c nu/nu, 6 week old, male), and then when a tumor volume reached at least 50 to 70 mm$^3$ (approx. 7 days), physiological saline (negative control), RLYE (SEQ ID NO: 2) (1.0 mg/kg), R(D)LYE (SEQ ID NO: 6) (1.0 mg/kg) or Ac-RLYE (SEQ ID NO: 1) (1.0 mg/kg; abnormal, experimental group) was intraperitoneally injected once a day. A VEGF neutralizing antibody, bevacizumab, was intraperitoneally injected at 2 mg/kg twice a week (positive control). A tumor size was two-dimensionally measured using calipers. A tumor volume (mm$^3$) was calculated by the formula: width$^2 \times$length$\times 0.52$.

1-6. Measurement of Tumor Angiogenesis

Tumor tissue was fixed with 10% formalin, and inserted into paraffin. A slide was prepared using a tumor tissue section, immersed in xylene to remove paraffin, and rehydrated by stepwise treatment with 100%, 95%, 80%, and 70% ethanol. Afterward, the slide was washed with deionized water several times at room temperature. To inhibit the intracellular activity of a peroxidase, the tissue section was reacted in 0.3% hydrogen peroxide-containing methanol for 15 minutes, and washed with PBS three times. The tissue section was reacted in 3% goat serum-containing PBS for 2 hours at room temperature, and reacted with FITC-isolectin B4 (5 mg/ml; Vector Laboratories) for 1 hour. The tissue section was washed with PBS three times and then a permanent slide was prepared using a cryo-mount solution (OCT mouting medium, Tissue Tek, Sakura Finetek), and then tumor vessels were visualized using a fluorescence microscope.

1-7. Measurement of Laser-Induced Choroidal Neovascularization

To prepare a laser-induced choroidal neovascularization animal model, a Bruch membrane between a retinal layer and a choroidal layer was destroyed by irradiating the mouse retina with a diode laser at an intensity of 400 mW and a duration of 50 ms, and then choroidal neovascularization occurred over 14 days. The retinas of 6 week-old male C57BL/6 mice were irradiated with a laser under the above conditions, the formation of a lesion was confirmed through a safety inspection on day 10, and 1 µl of a 1.5 mM EYLR (SEQ ID NO: 5), RLYE (SEQ ID NO: 2) or Ac-RLYE (SEQ ID NO: 1) solution was intravitreally injected. Here, the same amount of saline was injected into the control group. After 4 days (14 days after the laser irradiation), an experiment for analyzing a therapeutic effect was carried out by extracting the eyeballs of the mice. The extracted eyeballs were fixed in 4% paraformaldehyde for 12 hours, and embedded in paraffin. Sections with a thickness of 4 µm were prepared from paraffin tissue, and subjected to H&E staining. Afterward, an image of a section with the largest choroidal neovascular membrane area was taken from each subject, and the area of the choroidal neovascular membrane was quantitatively analyzed using ImageJ program (NIH, Bethesda, Md., USA). In the saline-injected control group, the average of the choroidal neovascular areas was represented as 100%, and a therapeutic effect of each treatment group was analyzed. Meanwhile, 1 ml (1.25 mg) of FITC-dextran (250 kDa) was injected into the left ventricle one hour before extraction of the mouse eyeball to allow systemic perfusion. After extraction, the eyeball was fixed in 4% paraformaldehyde for 1 hour. Then, the cornea and the crystalline lens were cut off by scissors, the retina was carefully removed using forceps to prepare a complex of retina pigment epithelium/choroid/sclera tissues. The retina flat-mounted complex tissue was observed under a fluorescence microscope and photographed.

1-8. Streptozotocin (STZ)-Induced Diabetic Retinopathy Mouse Model

A freshly prepared STZ solution (100 mM) in a citrate buffer (100 mM, pH 4.5) was intraperitoneally injected at 150 mg/kg into the mice, and to prevent hypoglycemic shock, 10% sucrose was sufficiently provided. After two days, blood glucose was measured using an Accu-Chek Performa blood glucose meter (Roche Diagnostics GmbH, Germany), and when non-fasting blood glucose within 1 to 2 weeks was maintained at 300 mg/dl or more, the mice were used as diabetic animal models. The diabetes-induced mice were anesthetized with 2% avertin, and 1 µl of a 1.5 mM EYLR (SEQ ID NO: 5), RLYE (SEQ ID NO: 2) or Ac-RLYE (SEQ ID NO: 1) solution was intravitreally injected. Here, the same amount of PBS was injected into the control group. The peptide was injected, and after 24 hours, 1 ml (1.25 mg) of FITC-dextran (250 kDa) was injected into the left ventricle of each mouse to allow circulation for approximately 5 minutes. The mice were euthanized by cervical dislocation, and the eyeballs were extracted and fixed in 4% paraformaldehyde at room temperature for 1 hour. The retina was isolated from the fixed eyeball to prepare a retinal flat mount, and vascular leakage was observed under a confocal microscope. Meanwhile, the fluorescence of FITC-dextran leaked from retinal vessels was measured using Fluoview software.

2. Experimental Results 2-1. Experiment for Stability of RLYE Peptide (SEQ ID NO: 2) in Human Serum and Analysis of Cause of Short Half-Life To evaluate RLYE (SEQ ID NO: 2) stability, an RLYE peptide (SEQ ID NO: 2) was added to each of PBS and human serum, and incubated by time at a constant temperature of 37° C. When RLYE (SEQ ID NO: 2) was incubated in PBS at a constant temperature, degradation of the RLYE peptide (SEQ ID NO: 2) did not occur, and when RLYE peptide (SEQ ID NO: 2) was incubated in human serum, the half-life of RLYE (SEQ ID NO: 2) was 1.2 hours (refer to FIG. 1 (A)).

Meanwhile, to identify which component in the human serum caused the stability of RLYE to decrease, a major component of serum, albumin, and inhibitors of various proteases were added to RLYE (SEQ ID NO: 2), followed by incubation at a constant temperature of 37° C. As a result, the albumin did not induce RLYE (SEQ ID NO: 2) degradation, and it was confirmed that RLYE (SEQ ID NO: 2) degradation due to human serum was not inhibited by treatment of aprotinin, EDTA, leupeptin and phenylmethyl sulfonyl fluoride (PMSF), which are known as protease inhibitors (refer to FIG. 1 (B)). However, when aminopeptidase B inhibitor, bestatin, was added, it was confirmed that RLYE (SEQ ID NO: 2) degradation by the human serum was effectively inhibited (refer to FIG. 1 (C)). Such results suggest that RLYE (SEQ ID NO: 2) was degraded by aminopeptidase B present in the serum.

Figure 2:
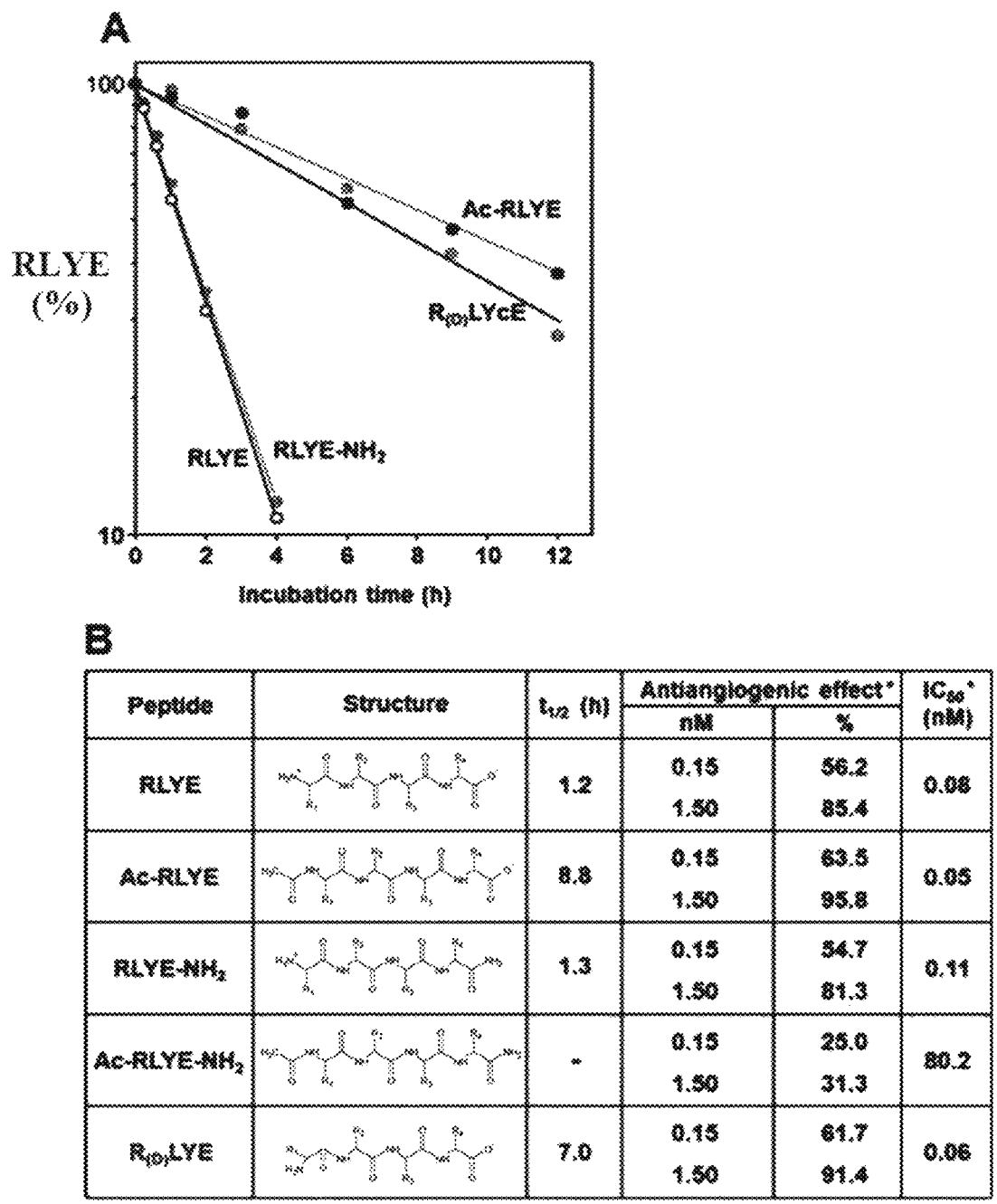
FIG. 2 shows experimental results showing effects of RLYE (SEQ ID NO: 2) and modified RLYEs ("RLYE" disclosed as SEQ ID NO: 2) on stability in human serum and migration of vascular endothelial cells. A: An experimental result showing the stability of RLYE (SEQ ID NO: 2) and modified RLYEs ("RLYE" disclosed as SEQ ID NO: 2) (Ac-RLYE (SEQ ID NO: 1), RLYE-NH$_2$ (SEQ ID NO: 3), Ac-RLYE-NH$_2$ (SEQ ID NO: 4), and R(D)LYE (SEQ ID NO: 6)) in human serum, B: An experimental result showing effects of RLYE (SEQ ID NO: 2) and modified RLYEs ("RLYE" disclosed as SEQ ID NO: 2) on half-life (t½) in human serum and inhibition (IC50) to migration of vascular endothelial cells. (B: Discloses SEQ ID NOS 2, 1, 3-4 and 6, respectively, in order of appearance.)

2-2. Studies on Stability and Pharmacological Activity of RLYE and RLYE N/C-Terminus-Modified Peptide in Human Serum To evaluate the stability of RLYE (SEQ ID NO: 2) and modified RLYE (SEQ ID NO: 2) (Ac-RLYE (SEQ ID NO:

1), RLYE-NH$_2$ (SEQ ID NO: 3), Ac-RLYE-NH$_2$ (SEQ ID NO: 4) or R(D)LYE (SEQ ID NO: 6)), the RLYE (SEQ ID NO: 2) and modified RLYE (SEQ ID NO: 2) were incubated in human serum for 12 hours at a constant temperature of 37° C. As a result, the half-life of RLYE (SEQ ID NO: 2) and RLYE-NH$_2$ (SEQ ID NO: 3) was 1.2 hours and 1.3 hours, respectively, and the half-life of Ac-RLYE and R(D)LYE peptides ("Ac-RLYE" and R(D)LYE" disclosed as SEQ ID NOS 1 and 6, respectively) were 8.8 hours and 7.0 hours, respectively (refer to FIG. 2 (A)).

To confirm the pharmacological effects of RLYE (SEQ ID NO: 2) and modified RLYE (SEQ ID NO: 2), effects on vascular endothelial cell migration, one of the typical phenomena of angiogenesis, were studied. Under a condition in which HUVECs were treated with VEGF and migration of vascular endothelial cells was induced, each peptide was added, and the IC50 value for inhibition of the cell migration was measured. As a result, IC50 values of RLYE (SEQ ID NO: 2), Ac-RLYE (SEQ ID NO: 1), RLYE-NH$_2$ (SEQ ID NO: 3), Ac-RLYE-NH$_2$ (SEQ ID NO: 4) and R(D)LYE (SEQ ID NO: 6) were 0.08, 0.05, 0.11, 80.2 and 0.06 nM, respectively, and it was confirmed that the angiogenesis inhibitory effects of Ac-RLYE (SEQ ID NO: 1) and R(D)LYE (SEQ ID NO: 6) were similar to or a little better than that of RLYE (SEQ ID NO: 2) which was confirmed to have an angiogenesis inhibitory effect at an early stage (refer to FIG. 2 (B)). Such results show that, when RLYE (SEQ ID NO: 2) was modified into Ac-RLYE (SEQ ID NO: 1) and R(D)LYE (SEQ ID NO: 6), the stability of the peptide was increased, and the migration of endothelial cells can be effectively inhibited.

Figure 3:
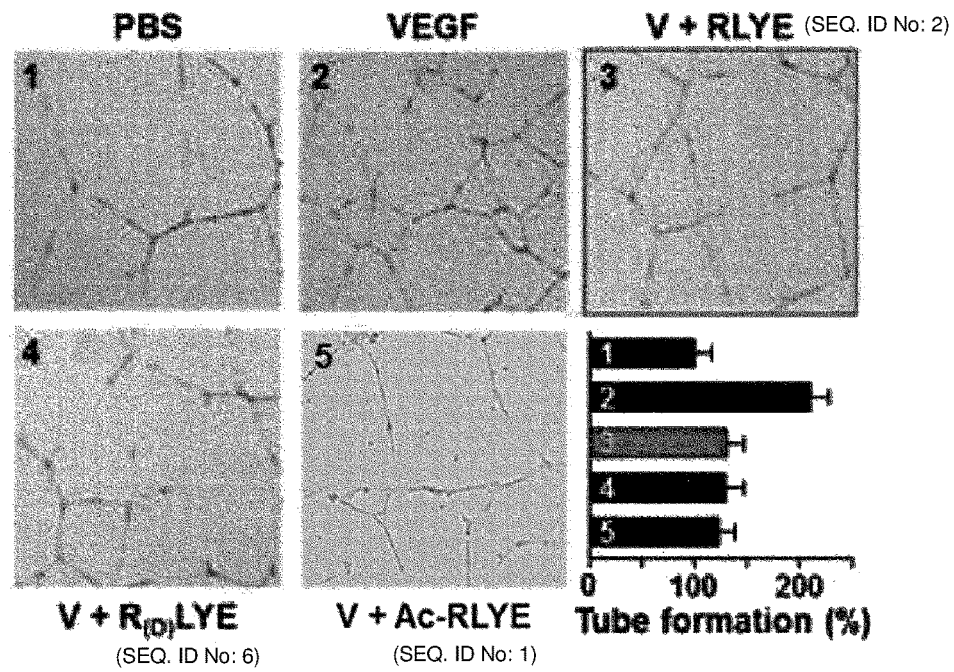
FIG. 3 shows experimental results showing effects of RLYE (SEQ ID NO: 2), Ac-RLYE (SEQ ID NO: 1) and R(D)LYE (SEQ ID NO: 6) on tube formation of vascular endothelial cells depending on pretreatment of human serum. A: An experimental result showing an effect of a peptide pretreated with phosphate-buffered saline (PBS) for three hours on tube formation of vascular endothelial cells induced by VEGF(V), B: An experimental result showing an effect of a peptide pretreated with human serum for three hours on tube formation of vascular endothelial cells induced by VEGF(V).
Figure 3:
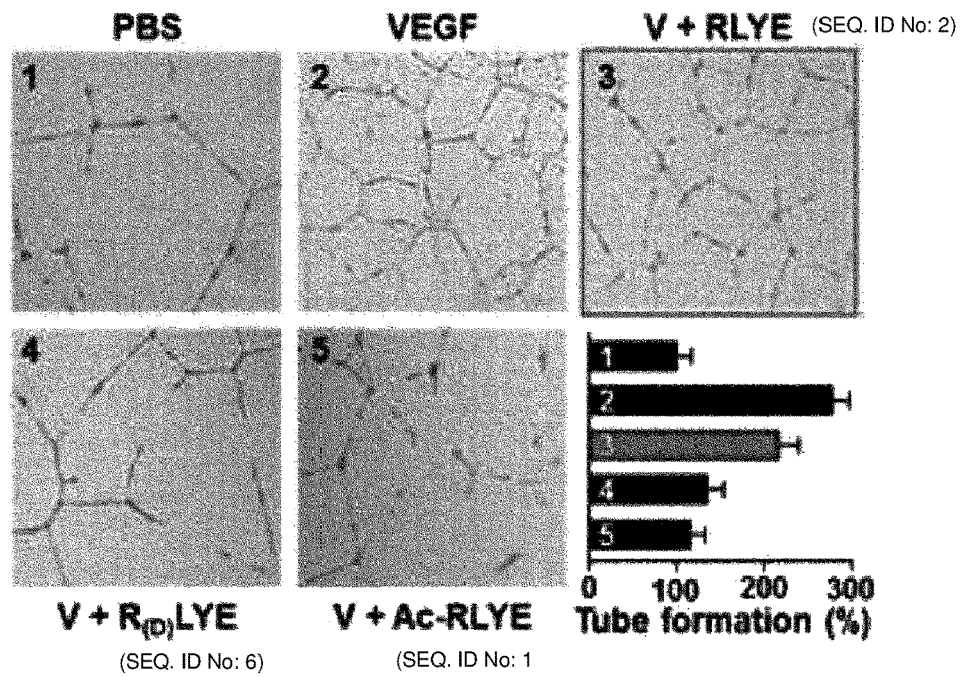

2-3. Study on Pharmacological Activity of RLYE (SEQ ID NO: 2), Ac-RLYE (SEQ ID NO: 1) and R(D)LYE (SEQ ID NO: 2) According to Absence or Presence of Serum Angiogenesis is very important not only in the proliferation and migration of vascular endothelial cells, but also the morphological differentiation related to the tube formation of endothelial cells. Therefore, RLYE (SEQ ID NO: 2), Ac-RLYE (SEQ ID NO: 1) and R(D)LYE (SEQ ID NO: 6) were incubated in each of PBS and human serum for 3 hours at a constant temperature, and then effects of RLYE (SEQ ID NO: 2), Ac-RLYE (SEQ ID NO: 1) and R(D)LYE (SEQ ID NO: 6) on the tube formation of vascular endothelial cells were investigated using two-dimensional Matrigel. When these peptides were pretreated with PBS, the tube formation induced by VEGF was effectively inhibited, and inhibitory effects were similarly exhibited in all three types of peptides (refer to FIG. 3 (A)). Meanwhile, when these peptides were pretreated with human serum for three hours, Ac-RLYE (SEQ ID NO: 1) and R(D)LYE (SEQ ID NO: 6) effectively inhibited the tube formation of endothelial cells, but RLYE (SEQ ID NO: 2) insignificantly inhibited the tube formation (refer to FIG. 3 (B)). Such results suggest that, due to low RLYE (SEQ ID NO: 2) stability in blood, a pharmacological effect was reduced, and due to high stability of Ac-RLYE (SEQ ID NO: 1) and R(D)LYE (SEQ ID NO: 6), the pharmacological effect is sustained. As a result, the effect of modified RLYE (SEQ ID NO: 2) in a living body in which blood is present will be very high.

Figure 4:
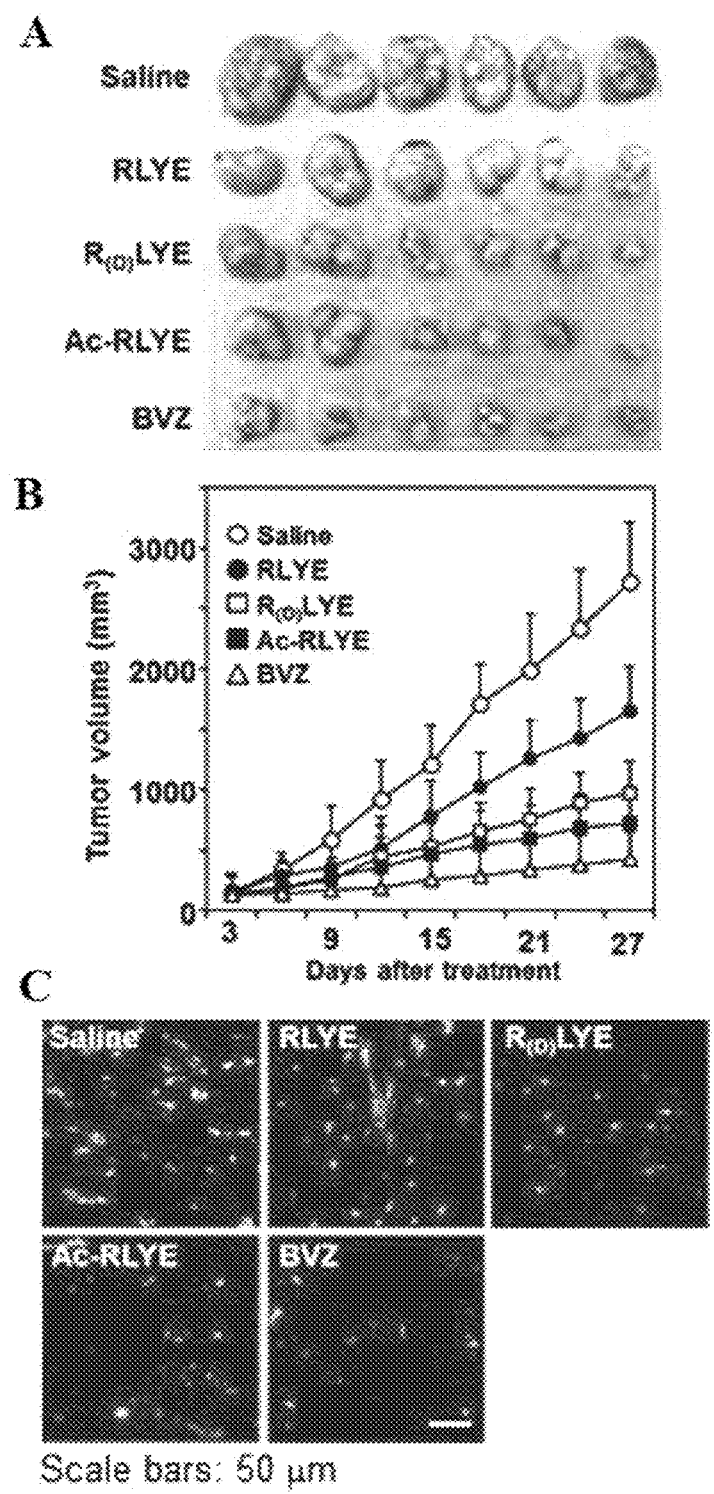
FIG. 4 shows effects of RLYE (SEQ ID NO: 2), Ac-RLYE (SEQ ID NO: 1) and R(D)LYE (SEQ ID NO: 6) on inhibition of tumor growth in human colorectal cancer cell-implanted mouse models. A: An experimental result showing an effect of administration of a peptide or bevacizumab (BVZ) on a tumor size (for 30 days after tumor induction), B: An experimental result showing an effect of administration of a peptide or bevacizumab (BVZ) on inhibition of tumor growth (for 30 days after tumor induction), C: An experimental result showing an effect of administration of a peptide or bevacizumab (BVZ) on inhibition of tumor angiogenesis.
Figure 5:
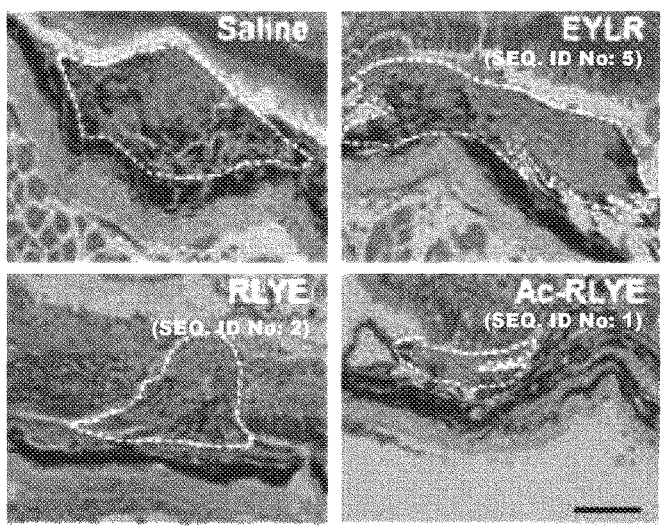
FIG. 5 shows experimental results showing effects of RLYE (SEQ ID NO: 2) and Ac-RLYE (SEQ ID NO: 1) on inhibition of choroidal neovascularization in laser-induced choroidal neovascularization mouse models. A: An experimental result showing an effect of a peptide on inhibition of choroidal neovascularization, detected by hematoxylin-eosin (H&E) staining (parts shown by a dotted line represent the boundary of a choroidal neovascularization lesion), B: A quantitative analysis result for the area of choroidal neovascularization, C: An experimental result showing an effect of a peptide on inhibition of choroidal neovascularization in retinal pigment epithelium/choroid/sclera complex tissue of an eyeball extracted after intravenous injection of fluorescein isothiocyanate (FITC)-binding dextran. (A, B and C also disclose "EYLR" as SEQ ID NO: 5.)
Figure 5:
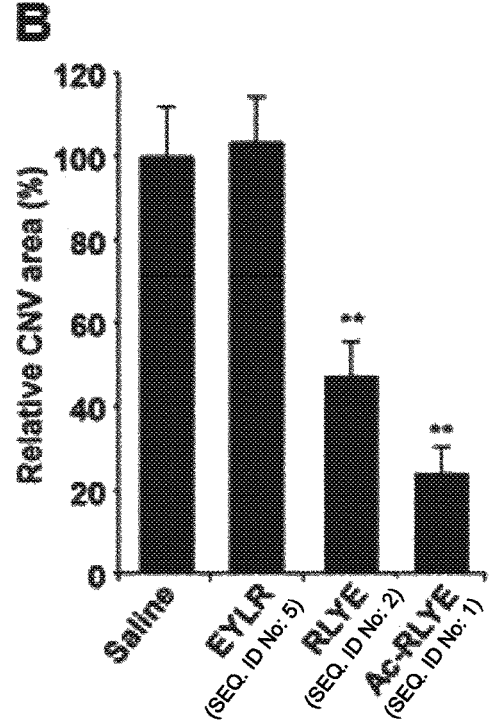
Figure 5:
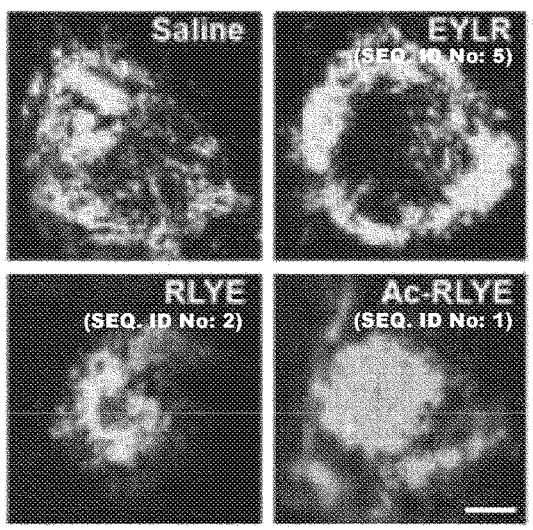

2-4. Study on Anticancer Effects of RLYE (SEQ ID NO: 2), Ac-RLYE (SEQ ID NO: 1) and R(D)LYE (SEQ ID NO: 6) in Mouse Tumor Models To investigate anticancer effects of RLYE (SEQ ID NO: 2), Ac-RLYE (SEQ ID NO: 1) and R(D)LYE (SEQ ID NO: 6) in human colon cancer cell (HCT116)-xenografted nude mouse models, each peptide was injected into the peritoneal cavity once a day at a dose of 1.0 mg/kg/day, and 2.0 mg/kg of a clinically-used VEGF neutralizing antibody anticancer agent, bevacizumab (Avastin), as a positive control, was intraperitoneally injected twice a week. As a result, it was seen that these peptides inhibited the size and growth of a tumor, and the anticancer effects of Ac-RLYE (SEQ ID NO: 1) and R(D)LYE (SEQ ID NO: 6) are higher than that of RLYE (SEQ ID NO: 2) (refer to FIGS. 4 (A and B)). The anticancer effects of Ac-RLYE (SEQ ID NO: 1) and R(D)LYE (SEQ ID NO: 6) were a little lower than that of the positive control bevacizumab. By a result of staining blood vessels generated in tumor tissue with FITC-isolectin B4, it was confirmed that the effects of inhibiting cancer angiogenesis by Ac-RLYE (SEQ ID NO: 1) and R(D)LYE (SEQ ID NO: 6) were higher than that of RLYE (SEQ ID NO: 2) (refer to FIG. 4 (C)). Such results show that the anticancer effects of Ac-RLYE (SEQ ID NO: 1) and R(D)LYE (SEQ ID NO: 6) prepared by modifying the N-terminal amino acid L-arginine (R) of RLYE (SEQ ID NO: 2) were increased due to high stability in a living body and thereby effective inhibition of cancer angiogenesis.

Figure 6:
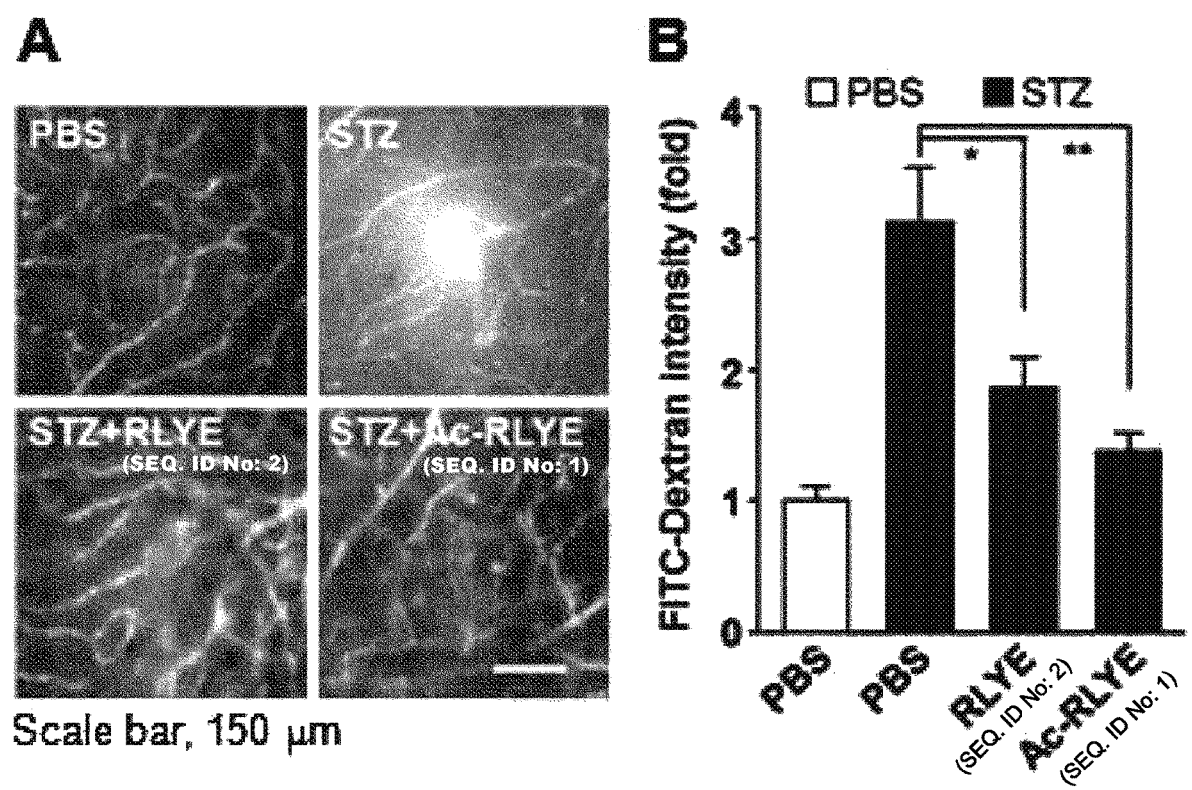
FIG. 6 shows experimental results showing effects of RLYE (SEQ ID NO: 2) and Ac-RLYE (SEQ ID NO: 1) on inhibition of retinal vascular leakage in diabetic mouse models. A: An experimental result showing an effect of a peptide on inhibition of retinal vascular leakage due to diabetes induced by streptozotocin (STZ). B: An experimental result showing an effect of a peptide on inhibition of retinal vascular leakage due to diabetes.

2-5. Study on Inhibitory Effects of RLYE (SEQ ID NO: 2) and Ac-RLYE (SEQ ID NO: 1) on Laser-Induced Choroidal Angiogenesis For the development of a therapeutic agent for a refractory eye disease such as senile macular degeneration (wet-AMD or neovascular AMD), a laser-induced choroidal neovascularization inhibitory effect is generally studied in mouse models. Each peptide was added to laser-induced choroidal neovascularization in mice, and its choroidal neovascularization inhibitory effect was confirmed, and thereby EYLR (SEQ ID NO: 5) (reverse-sequence of the RLYE peptide (SEQ ID NO: 2)) had no change in the occurrence of choroidal neovascularization, but when RLYE (SEQ ID NO: 2) and Ac-RLYE (SEQ ID NO: 1) were added, the choroidal neovascularization was effectively reduced, and Ac-RLYE (SEQ ID NO: 1) was highly effective compared to RLYE (SEQ ID NO: 2) (refer to FIGS. 6 (A and B)). In research using a retinal flat mount technique, it was also confirmed that Ac-RLYE (SEQ ID NO: 1) exhibited a higher effect of inhibiting choroidal neovascularization than RLYE (SEQ ID NO: 2) (refer to FIG. 6 (C)). Such results suggest that RLYE (SEQ ID NO: 2) N-terminus modified Ac-RLYE (SEQ ID NO: 1) can be used as a therapeutic agent for senile macular degeneration related to angiogenesis.

2-6. Study on Therapeutic Effects of RLYE (SEQ ID NO: 2) and Ac-RLYE (SEQ ID NO: 1) on Diabetic Retinopathy It was confirmed that retinal vascular leakage was considerably increased in mouse models in which diabetic retinopathy was induced by administering streptozotocin (STZ), and the administration of RLYE (SEQ ID NO: 2) and Ac-RLYE (SEQ ID NO: 1) effectively inhibited the retinal vascular leakage (refer to FIGS. 6 (A and B)). Meanwhile, as comparing inhibitory effects of these two peptides on retinal vascular leakage, it was confirmed that Ac-RLYE (SEQ ID NO: 2) exhibited a higher inhibitory effect on blood vascular leakage than RLYE (SEQ ID NO: 2). Such results suggest that Ac-RLYE (SEQ ID NO: 1) which effectively inhibits retinal vascular leakage occurring in a diabetic related disease can be used as a therapeutic agent for diabetic retinopathy.

REFERENCES

International Patent Publication No. WO 97/41824

G. Neufeld, T. Cohen, S. Gengrinovitch, Z. Poltorak, Vascular endothelial growth factor (VEGF) and its receptors, FASEBJ. 13 (1999) 9-22.

J. Folkman, Angiogenesis in cancer, vascular, rheumatoid and other disease, Nat. Med. 1 (1995) 27-31.

R. H. Adams, K. Alitalo, Molecular regulation of angiogenesis and lymphangiogenesis, Nat. Rev. Mol. Cell Biol. 8 (2007) 8464-8478.

N. Ferrara, H. P. Gerber, J. LeCouter, The biology of VEGF and its receptors, Nat. Med. 9 (2003) 669-676.

N. Ferrara, R. S. Kerbel, Angiogenesis as a therapeutic target, Nature 438 (2005) 967-74.

H. Takahashi, M. Shibuya, The vascular endothelial growth factor (VEGF)/VEGF receptor system and its role under physiological and pathological conditions, Clin. Sci. (Lond) 109 (2005) 227-241.

M. Shibuya, VEGF-VEGFR Signals in Health and Disease, Biomol. Ther. (Seoul) 22 (2014) 1-9.

F. M. Yakes, J. Chen, J. Tan, K. Yamaguchi, Y. Shi, P. Yu, F. Qian, F. Chu, F. Bentzien, B. Cancilla, J. Orf, A. You, A. D. Laird, S. Engst, L. Lee, J. Lesch, Y. C. Chou, A. H. Joly, Cabozantinib (XL184), a novel MET and VEGFR2 inhibitor, simultaneously suppresses metastasis, angiogenesis, and tumor growth, Mol. Cancer Ther. 10 (2011) 2298-2308.

S. R. Wedge, D. J. Ogilvie, M. Dukes, J. Kendrew, R. Chester, J. A. Jackson, S. J. Boffey, P. J. Valentine, J. O. Curwen, H. L. Musgrove, G. A. Graham, G. D. Hughes, A. P. Thomas, E. S. Stokes, B. Curry, G. H. Richmond, P. F. Wadsworth, A. L. Bigley, L. F. Hennequin, ZD6474 inhibits vascular endothelial growth factor signaling, angiogenesis, and tumor growth following oral administration, Cancer Res. 62 (2002) 4645-4655.

W. K. You, B. Sennino, C. W. Williamson, B. Falcon, H. Hashizume, L. C. Yao, D. T. Aftab, D. M. McDonald, VEGF and c-Met blockade amplify angiogenesis inhibition in pancreatic islet cancer, Cancer Res. 71(2011) 4758-4768.

D. D. Hu-Lowe, H. Y. Zou, M. L. Grazzini, M. E. Hallin, G. R. Wickman, K. Amundson, J. H. Chen, D. A. Rewolinski, S. Yamazaki, E. Y. Wu, M. A. McTigue, B. W. Murray, R. S. Kania, P. O'Connor, D. R. Shalinsky, S. L. Bender, Nonclinical antiangiogenesis and antitumor activities of axitinib (AG-013736), an oral, potent, and selective inhibitor of vascular endothelial growth factor receptor tyrosine kinases 1, 2, 3, Clin. Cancer Res. 14 (2008)7272-7283.

F. Hilberg, G. J. Roth, M. Krssak, S. Kautschitsch, W. Sommergruber, U. Tontsch-Grunt, P. Garin-Chesa, G. Bader, A. Zoephel, J. Quant, A. Heckel, W. J. Rettig, BIBF 1120: triple angiokinase inhibitor with sustained receptor blockade and good antitumor efficacy, Cancer Res. 68(2008) 4774-4782.

J. C. Soria, A. Mauguen, M. Reck, A. B. Sandler, N. Saijo, D. H. Johnson, D. Burcoveanu, M. Fukuoka, B. Besse, J. P. Pignon, Systematic review and meta-analysis of randomised, phase II/III trials adding bevacizumab to platinum-based chemotherapy as first-line treatment in patients with advanced non-small-cell lung cancer, Ann. Oncol. 24 (2013) 20-30.

S. J. Lee, S. Namkoong, Y. M. Kim, C. K. Kim, H. Lee, K. S. Ha, H. T. Chung, Y. G. Kwon, Y. M. Kim, Fractalkine stimulates angiogenesis by activating the Raf-1/MEK/ERK- and PI3K/Akt/eNOS-dependent signal pathways, Am. J. Physiol. Heart Circ. Physiol. 291 (2006) H2836-H2846.

J. H. So, S. K. Hong, H. T. Kim, S. H. Jung, M. S. Lee, J. H. Choi, Y. K. Bae, T. Kudoh, J. H. Kim, C. H. Kim, 2010. Gicerin/Cd146 is involved in zebrafish cardiovascular development and tumor angiogenesis. Genes Cells 15 (2010) 1099-110.

Y. Cao, A. Chen, S. S. A. An, R. W. Ji, D. Davidson, M. Llinas, Kringle 5 of plasminogen is a novel inhibitor of endothelial cell growth, J. Biol. Chem. 272 (1997) 22924-22928

P. C. Lee, A. N. Salyapongse, G. A. Bragdon, L. L. Shears 2nd, S. C. Watkins, H. D. Edington, T. R. Billiar, Impaired wound healing and angiogenesis in eNOS-deficient mice, Am. J. Physiol. 277 (1999) H1600-1608.

K. R. Kidd, B. M. Weinstein, Fishing for novel angiogenic therapies, Br. J. Pharmacol. 140 (2003) 585-594.

S. Isogai, M. Horiguchi, B. M. Weinstein, The vascular anatomy of the developing zebrafish: an atlas of embryonic and early larval development. Dev. Biol. 230 (2001) 278-301.

J. I. Greenberg, D. A. Cheresh, VEGF as an inhibitor of tumor vessel maturation: implications for cancer therapy, Expert Opin. Biol. Ther. 9 (2009) 1347-1356.

Idbaih, F. Ducray, M. Sierra Del Rio, K. Hoang-Xuan, J. Y. Delattre, Therapeutic application of noncytotoxic molecular targeted therapy in gliomas: growth factor receptors and angiogenesis inhibitors, Oncologist 13 (2008) 978-992.

K. M. Cook, W. D. Figg, Angiogenesis inhibitors: current strategies and future prospects, CA Cancer J. Clin. 60 (2010) 222-243.

H. M. Verheul, H. M. Pinedo, Possible molecular mechanisms involved in the toxicity of angiogenesis inhibition, Nat. Rev. Cancer 7 (2007) 475-485.

M. S. O'Reilly, L. Holmgren, Y. Shing, C. Chen, R. A. Rosenthal, M. Moses, W. S. Lane, Y. Cao, E. H. Sage, J. Folkman, Angiostatin: a novel angiogenesis inhibitor that mediates the suppression of metastases by a Lewis lung carcinoma, Cell 79 (1994) 315-328.

G. S. Sheppard, M. Kawai, R. A. Craig, D. J. Davidson, S. M. Majest, R. L. Bell, J. Henkin, Lysyl 4-aminobenzoic acid derivatives as potent small molecule mimetics of plasminogen kringle 5, Bioorg. Med. Chem. Lett. 14 (2004) 965-966.

Y. Wang, D. Fei, M. Vanderlaan, A. Song, Biological activity of bevacizumab, a humanized anti-VEGF antibody in vitro, Angiogenesis 7 (2004) 335-345.

The invention claimed is:

1. A peptide for inhibiting angiogenesis consisting of the amino acid sequence Arg-Leu-Tyr-Glu (SEQ. ID NO: 1), in which N-terminal L-Arg is acetylated.

2. The peptide of claim 1, wherein the peptide inhibits angiogenesis induced by a vascular endothelial growth factor (VEGF).

3. A method of inhibiting angiogenesis in a subject in need thereof, the method comprising administering the peptide of claim 1 as an active ingredient to the subject.

4. A method for treating angiogenesis, comprising administering the peptide of claim 1 to a subject in need thereof.

5. A method for treating melanoma or colorectal cancer, comprising administering the peptide of claim 1 to a subject in need thereof.

6. A method for treating diabetic retinopathy, comprising administering the peptide of claim 1 to a subject in need thereof.

7. A method for treating senile macular degeneration, comprising administering the peptide of claim 1 to a subject in need thereof.

8. A peptide for inhibiting angiogenesis consisting of the amino acid sequence Arg-Leu-Tyr-Glu (SEQ. ID NO: 6), in which L-Arg is substituted with D-Arg.

9. The peptide of claim 8, which inhibits angiogenesis induced by a vascular endothelial growth factor (VEGF).

10. A method of inhibiting angiogenesis in a subject in need thereof, the method comprising administering the peptide of claim 8 as an active ingredient to the subject.

11. A method for treating melanoma or colorectal cancer, comprising administering the peptide of claim 8 to a subject in need thereof.

12. A method for treating diabetic retinopathy, comprising administering the peptide of claim 8 to a subject in need thereof.

13. A method for treating senile macular degeneration, comprising administering the peptide of claim 8 to a subject in need thereof.

* * * * *

SEQUENCE LISTING

<160> NUMBER OF SEQ ID NOS: 6

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Arg Leu Tyr Glu
1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Leu Tyr Glu
1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Leu Tyr Glu
1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Leu Tyr Glu
1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Glu Tyr Leu Arg
1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<221> NAME/KEY: MOD_RES
<222> LOCATION: (1)..(1)
<223> OTHER INFORMATION: D-Arg

<400> SEQUENCE: 6

Arg Leu Tyr Glu
1
```